(12) United States Patent
Vaughn

(10) Patent No.: US 9,649,289 B1
(45) Date of Patent: May 16, 2017

(54) METHOD AND COMPOSITION FOR TREATING DYSBIOSIS AND RELATED DISEASE STATES

(71) Applicant: BioAvivus, LLT, Champaign, IL (US)

(72) Inventor: Charles W. Vaughn, Urbana (IL)

(73) Assignee: BioAvivus, LLT, Champaign, IL (US)

( * ) Notice: Subject to any disclaimer, the term of this patent is extended or adjusted under 35 U.S.C. 154(b) by 0 days.

(21) Appl. No.: 15/237,706

(22) Filed: Aug. 16, 2016

(51) Int. Cl.
*A61K 31/235* (2006.01)
*A61K 31/618* (2006.01)
*A61K 9/14* (2006.01)
*A61K 9/00* (2006.01)

(52) U.S. Cl.
CPC .......... *A61K 31/235* (2013.01); *A61K 9/0053* (2013.01); *A61K 9/14* (2013.01)

(58) Field of Classification Search
CPC ....... A61K 31/235; A61K 9/14; A61K 9/0053
See application file for complete search history.

(56) References Cited

U.S. PATENT DOCUMENTS

| | | | |
|---|---|---|---|
| 5,225,201 A | 7/1993 | Beaurline | |
| 5,552,160 A | 9/1996 | Liversidge et al. | |
| 6,759,057 B1 | 7/2004 | Weiner et al. | |
| 8,865,187 B2 * | 10/2014 | Lichtenberger | A61K 9/107 424/400 |
| 2011/0064813 A1 | 3/2011 | Vaughn | |
| 2015/0010654 A1 * | 1/2015 | Arnold | A61K 9/0031 424/717 |

OTHER PUBLICATIONS

Damman, Salicylate and the microbiata: A new mechanistic understanding of an ancient drug's role in dermatological and gastrointestinal disease, Drug development research 74: 344-352 (2013).*
Cuomo et al, Irritable bowel syndrome and food interaction, World Journal of Gastroenterology, vol. 20, Issue 27, Jul. 21, 2014.*
Caraco Pharmaceutical Laboratories, Ltd, Salsalate Tablet, Issued Mar. 2008.*
Picco, M.D. Diseases and Conditions, GERD, Mayo Clinic. Published Jan. 2015.*
Shirakawa et al., "Salicylate, diflunisal and their metabolites inhibit CBP/p300 and exhibit anticancer activity", eLife 2016;5:31156. DOIG 10.7554/eLife.11156, Published May 31, 2016.
Pischon et al., "Plasma Adiponectin Levels and Risk of Myocardial Infarction in Men", JAMA, Apr. 14, 2004, vol. 291, No. 14, pp. 1730-1737.
Nohria et al., "Vascular Medicine: The Effect of Salsalate Therapy on Endothelial Function in a Broad Range of Subjects", J Am Heart Assoc., 2014: 3: e000609, originally published Jan. 3, 2014, doi: 10.1161/JAHA.113.000609.
Kennon et al., "The effect of aspirin on C-reactive protein as a marker of risk in unstable angina", J am Coll Cardiol., 2001;37(5):1266-1270, doi:10.1016/S0735-1097(01)01130-5.
"Dysbiosis." Wikipedia, https://en.wikipedia.org/wiki/Dysbiosis. Accessed Feb. 20, 2017.

* cited by examiner

*Primary Examiner* — Mina Haghighatian
(74) *Attorney, Agent, or Firm* — James G. Passé; Passé Intellectual Property, LLC

(57) ABSTRACT

The present invention is the treatment of dysbiosis and related disease states caused by or made worse by dysbiosis, using an oral treatment of nanosized salsalate particles.

4 Claims, 3 Drawing Sheets

METHOD AND COMPOSITION FOR TREATING DYSBIOSIS AND RELATED DISEASE STATES

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a treatment of dysbiosis, a treatment of disease states caused or made worse by the presence of dysbiosis, and a novel treatment composition. In particular, it relates to the use of a small particle size salsalate as a treatment for dysbiosis.

Description of Related Art

The human colonic microbiota is a highly complex microbial ecosystem, and several hundred different species of bacteria are known to colonize the gut. The homeostasis established between the human and the resident gut bacteria plays important functional roles, such as protection against pathogenic organisms, maturation and modulation of the immune system, intestinal maturation, production of short-chain fatty acids (SCFA), mucosal physiology, and the production of vitamins, such as vitamin K and biotin. Alterations in this homeostasis, called dysbiosis, have a profound impact on human health, as demonstrated in several gastrointestinal diseases, including inflammatory bowel diseases (IBD), irritable bowel syndrome (IBS), and colorectal cancer (CRC). For instance, in genetically predisposed subjects, bacterial dysbiosis, including a decrease of Firmicutes, could result in disordered innate immune reactions and lead to IBD. Dysbiosis most commonly involves the human digestive tract and is associated with numerous pathologies, including bowel disease, chronic fatigue syndrome, myalgic encepthalomyelitis/chronic fatigue syndrome, obesity, bacterial vaginosis related cancer, nonalcoholic steatohepatitis (NASH), sleep disorders, atopic dermatitis, hypertension associated with obstructive sleep apnea, cardiovascular inflammation associated with obstructive sleep apnea, enteritis-related arthritis, sleep disorder, and celiac disease ("Reduced diversity and altered composition of the gut microbiome in individuals with myalgic encephalomyelitis/chronic fatigue syndrome;" Gilotreaux, L. et al.s Microbiome 2016).

Bacterial dysbiosis is related to many different kinds of pathologies. The clearest correlation between dysbiosis and disease was found with inflammatory bowel diseases (IBD), wherein the proportion of Firmicutes, in particular *Faecalibacterium prausnitzii* (F.p.), was found to be low in patients that exhibited endoscopic recurrence six months after surgery. IBD, including Crohn's disease and ulcerative colitis, are characterized by an abnormal activation of the immune system associated with the gut, resulting in a chronic inflammation of the digestive system. Therefore, treatment and correction of dysbiosis could be of immense benefit to treating those disease states which are caused by or made worse by a patient having dysbiosis due, in main part, to decreased levels of F.p.

Salsalate is a medication that belongs to the salicylate and non-steroidal anti-inflammatory drug (NSAID) classes. Relative to other NSAIDs, salsalate has a weak inhibitory effect on the cyclooxygenase enzyme and decreases the production of several proinflammatory chemical signals, such as interleukin 6 (IL-6), tumor necrosis factor alpha (TNF-alpha), and C-reactive protein (CRP). The mechanism through which salsalate is thought to reduce the production of these inflammatory chemical signals is through the inhibition of kappa B (κB) kinase, resulting in decreased action of NF-κB targeted genes. This mechanism is thought to be responsible for salsalate's insulin-sensitizing and blood sugar lowering properties. Known formulations of salsalate have an average particle size of at least around 40 microns (or more) based on the current technology for the production of salsalate.

BRIEF SUMMARY OF THE INVENTION

The present invention relates to the discovery that a nanosized salsalate, having a particle size of less than about 10 nm, is capable of treating intestinal dysbiosis, restoring to balance the imbalance of the gut microbiota, and providing homeostasis to the various microbes responsible for dysbiosis. The treatment of dysbiosis, therefore, treats the various disease states that are caused by or made worse by the patient having dysbiosis of the gut. Decreasing the particle size of salsalate has the added benefit of reducing the dosages needed and, thus, reducing the expected side effect of the administration of salsalate. Nanosizing also improves the bio-availability of salsalate, therein improving the onset of action of salsalate from four-times daily to once daily dosing.

Accordingly, in one embodiment, there is a method for treating dysbiosis and disease states caused or made worse by dysbiosis in a patient comprising administering to the patient with dysbiosis a pharmaceutically acceptable oral dosage of salsalate, having a particle size of less than about 10 microns sufficient to treat the patient's condition.

In another embodiment, there is an oral pharmaceutical composition comprising a pharmaceutically acceptable dosage of salsalate, having a particle size of less than about 10 microns.

DETAILED DESCRIPTION OF THE INVENTION

Figure 1:
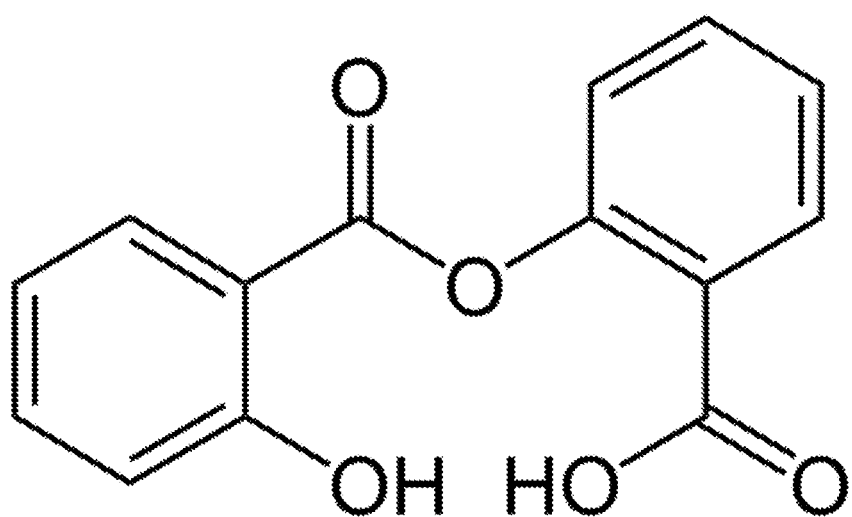
FIG. 1 is the structure of salsalate.

While this invention is susceptible to embodiment in many different forms, there is shown in the drawings, and will herein be described in detail, specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "about" and "essentially" mean±10 percent.
The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language, and is so intended.

References throughout this document to "one embodiment", "certain embodiments", and "an embodiment" or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitations thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein, the term "dysbiosis" refers to an imbalance in the intestinal microbiota of the type known to impact human health, to cause or make worse certain disease states and to upset the natural workings of the body. Natural workings of the body include modulation of the immune system, intestinal maturation, production of short chain fatty acids, mucosal physiology, and the production of vitamins, including Vitamin K and biotin. In other words, when there is a case of dysbiosis, certain diseases may be caused by, or made worse, by such condition. These include, but are not limited to, bowel disease, chronic fatigue syndrome, obesity, bacterial vaginitis related cancer, antibiotic resistance development, nonalcoholic steatohepatitis (NASH), sleep disorder, gastro esophageal reflux disease (GERD), atopic dermatitis, hypertension associated with obstructive sleep apnea, cardiovascular inflammation associated with obstructive sleep apnea, enteritis-related arthritis, and celiac disease. It also includes Irritable bowel syndrome, colitis and colorectal cancer.

As used herein, the term "treating" refers to "administering" (i.e. giving orally) the salsalate of the invention sufficient in the amount to treat a patient with dysbiosis, to treat the natural microbiota, and/or to treat disease states associated with or caused by such patient conditions. The oral "dosage" is sufficient in amount and time to restore the microbiota, in general from at least about 25 mg to about 500 mg, 750 mg or 1500 mg per day of the salsalate of the invention. In one embodiment, the daily dosage is about 50-150 mg per day—in another embodiment, the daily dosage is from about 75 mg to about 100 mg. Salsalate has been micronized to 2.4 microns for an average daily dose of 750 mg once daily (or less), and an increase in the rate of onset from three to four times to a therapeutic blood level within day one of initial therapy. In one embodiment, the daily dose is no more than about 750 mg, 500 mg, 300 mg, or 100 mg.

As used herein, the term "salsalate" refers to a pharmaceutically acceptable oral formulation having a particle size of from about 0.01 microns to about 10 microns. An average particle size, in one embodiment, is about 2.5 microns.

The scope of the present invention includes mixtures of stereoisomers, as well as purified enantiomers or enantiomerically/diastereomerically enriched mixtures. Also included within the scope of the invention are the individual isomers of the compounds of the present invention, as well as any wholly or partially equilibrated mixtures thereof. The present invention also includes the individual isomers of the compounds represented by the formulas above as mixtures with isomers, in which one or more chiral centers are inverted.

Typically, but not absolutely, the compounds herein include the salts of the present compositions and include the pharmaceutically acceptable salts. Salts encompassed within the term "pharmaceutically acceptable salts" refer to nontoxic salts of the compounds of this invention. Salts of the compounds of the present invention may include acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, thethiodide, thmethylammonium, and valerate salts. Other salts, which are not pharmaceutically acceptable, may be useful in the preparation of compounds of this invention, and these should be considered to form a further aspect of the invention.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. A therapeutically effective amount will produce a "therapeutic effect."

For use in therapy, therapeutically effective amounts of a compound of the present invention, as well as salts thereof, are presented as a pharmaceutical composition formulated to release in a colon-targeted delivery system.

The present invention provides pharmaceutical compositions that include effective amounts of a compound as herein described, or a salt thereof, and one or more pharmaceutically acceptable carriers, diluents, or excipients. The carrier(s), diluent(s), or excipient(s) must be acceptable, in the sense of being compatible with the other ingredients of the formulation and not deleterious to the recipient of the pharmaceutical composition and consistent with the mode of administration, i.e., oral or rectal.

In accordance with another aspect of the invention, there is also provided a process for the preparation of a pharmaceutical formulation, including admixing a compound of the present invention or salts thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation and the like are all factors to be considered. The therapeutically effective amount ultimately should be at the discretion of the attendant, physician, or veterinarian. Regardless, an effective amount of a salsalate of the present invention for the treatment of humans suffering from dysbiosis, generally, should be in the range of about 0.01 to about 5 mg/kg body weight of recipient (mammal) per day. More often, the effective amount should be in the range of 0.3 to 0.10 mg/kg body weight per day.

Pharmaceutical formulations may be presented in unit dose forms containing a predetermined amount of active ingredient per unit dose. Such a unit may contain, as a non-limiting example, 0.5 mg to 1.5 g of a compound of the present invention, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art and administered as oral formulations.

The compounds of the present invention, or a salt thereof, may be employed alone or in combination with other therapeutic agents. The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration in combination with a compound of the present invention or a salt or solvate thereof with other treatment agents may be in combination by administration concomitantly in: (1) a unitary pharmaceutical composition, including both compounds; or (2) separate pharmaceutical compositions, each including one of the compounds. Alternatively, the combination may be administered separately in a sequential manner, wherein one treatment agent is administered first and the other second or vice versa. Such sequential administration may be close in time or remote in time.

EXAMPLE AND DRAWINGS

Preparation of Small Micron Sized Particle Salsalate

Figure 2:
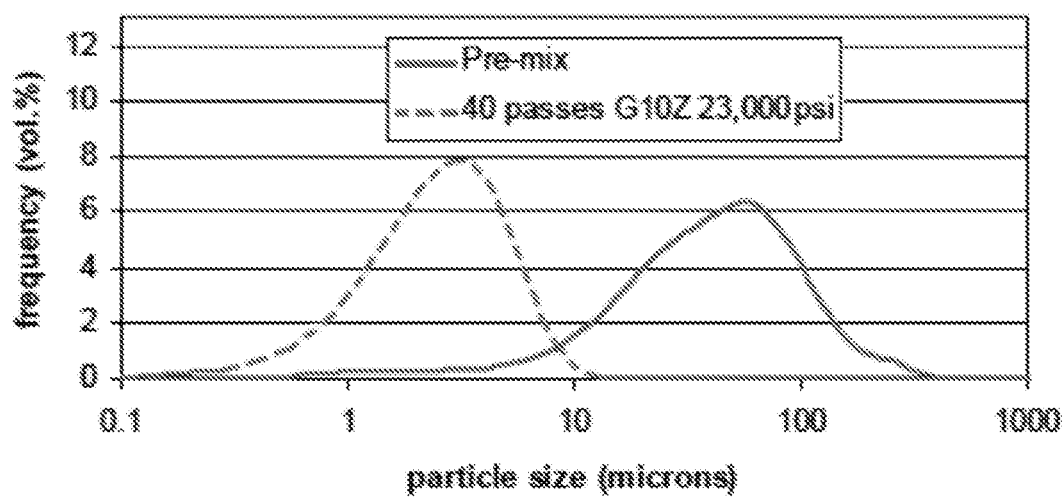
FIG. 2 is a comparison of the particle size of the present invention compared to previous compositions of salsalate.
Figure 3:
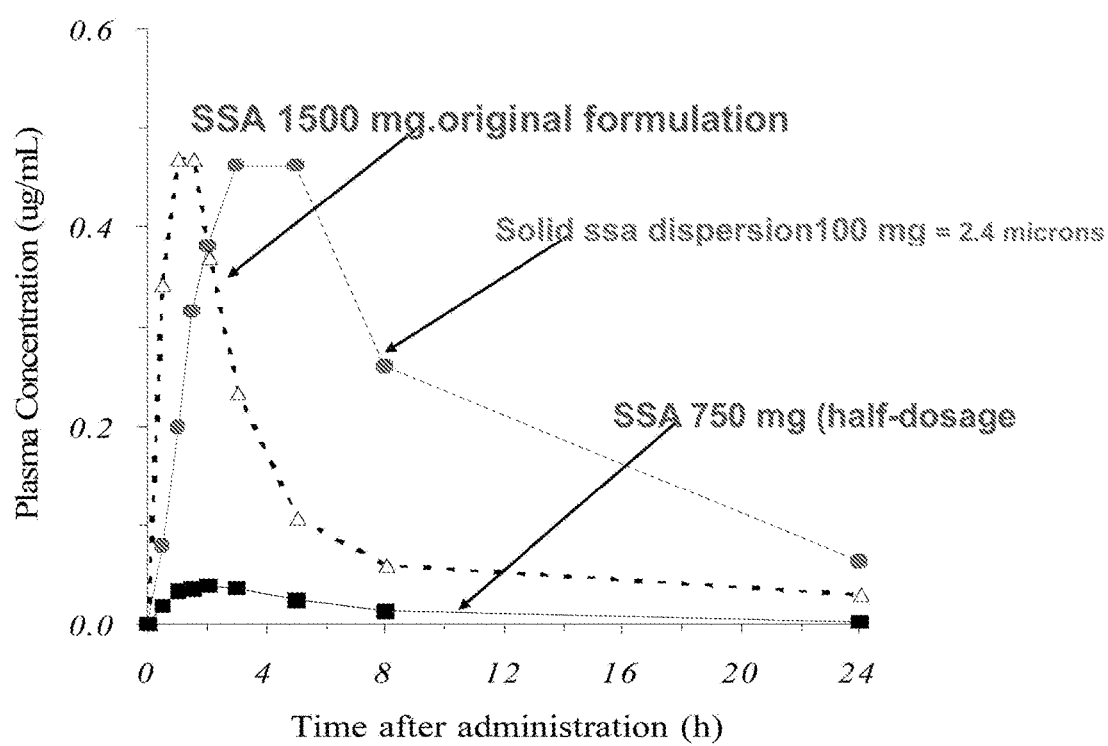
FIG. 3 is an oral bioavailability chart.

Using a Microfluidics® Homogenizer 40, passes with the device take the median particle size of salsalate FIG. 1 from about 40 microns down to about 2.4 microns, as shown in FIG. 2. The resulting salsalate is formulated into unit dose oral dosages, as noted above. FIG. 3 shows a bioavailability chart comparing regular salsalate with the formulation of the present invention.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A method for treating a patient diagnosed with dysbiosis of the intestinal microbiota, comprising administering to the patient with dysbiosis a pharmaceutically acceptable oral dosage of salsalate having a particle size of between about 0.1 microns and about 10 microns sufficient to return the balance of microbiota of the patient to normal.

2. The method according to claim 1 wherein the salsalate has an average particle size of about 2.5 microns.

3. The method according to claim 1 wherein the dosage of salsalate is from at least 25 mg to about 750 mg/day.

4. The method according to claim 3 wherein the dosage of salsalate is about 500 mg/day or less.

\* \* \* \* \*